United States Patent [19]

Elslager

[11] 3,963,740
[45] June 15, 1976

[54] BENZO AND BENZOTHIOPYRANOINDAZOLE N-OXIDES

[75] Inventor: Edward Faith Elslager, Ann Arbor, Mich.

[73] Assignee: Parke, Davis & Company, Detroit, Mich.

[22] Filed: Sept. 20, 1974

[21] Appl. No.: 507,634

Related U.S. Application Data

[63] Continuation-in-part of Ser. No. 379,779, July 16, 1973, abandoned.

[52] U.S. Cl.............................. 260/310 C; 260/311; 424/273
[51] Int. Cl.[2]............... C07D 231/56; A61K 31/415
[58] Field of Search....................... 260/310 C, 311

[56] References Cited
UNITED STATES PATENTS 2,500,131   3/1950   Linsker.............................. 260/279

FOREIGN PATENTS OR APPLICATIONS 1,816,086   8/1969   Germany........................... 260/310

*Primary Examiner*—Donald B. Moyer

[57] ABSTRACT

2H(1)Benzothiopyrano[4,3,2-cd]indazole N-oxides, 2H(1)benzopyrano[4,3,2-cd]indazole N-oxides and acid addition salts thereof are disclosed. These compounds can be produced by oxidation of the corresponding amines with oxidizing agents capable of forming an N-oxide derivative. The compounds are parasiticidal agents useful in the treatment of schistosome infections.

8 Claims, No Drawings

BENZO AND BENZOTHIOPYRANOINDAZOLE N-OXIDES

SUMMARY AND DETAILED DESCRIPTION

This invention is concerned with 2H(1)benzothiopyrano[4,3,2-cd]indazole N-oxides, 2H(1)benzopyrano[4,3,2-cd]indazole N-oxides, and acid addition salts thereof, their synthesis, pharmaceutical compositions containing them and their use in medicine.

It has been found that the compounds of formula (I)

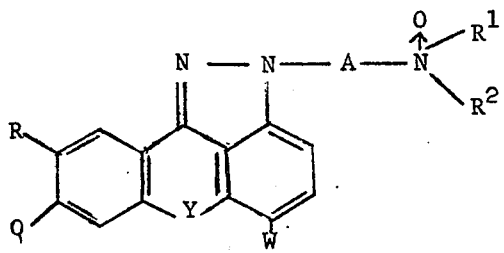

and acid addition salts thereof; wherein:

A is an alkylene radical containing 2 to 4 carbon atoms;

$R^1$ and $R^2$ are the same or different and represent $C_1 - C_4$ alkyl or together a lower alkylene radical containing 4 to 8 carbon atoms, 4 to 6 of which are joined in a ring with the nitrogen atom;

W is methyl, hydroxymethyl or acyloxymethyl wherein said acyl fragment contains from one to eight carbon atoms;

Y is S or O; and one of Q and R is hydrogen and the other is selected from hydrogen and a substituent halo or alkoxy group having from one to four carbon atoms, are useful parasiticidal agents, and in particular are active against infections of the trematode *Schistosoma mansoni* in the mouse. Unexpectedly, the compounds of the invention are markedly less mutagenic than hycanthone and related or known to the art.

\* A schistosomicidal derivative of thioxanthen-9-one.

The compounds of formula (I) and their salts may be prepared by any methods known in the art for the synthesis of compounds of analogous chemical structure. For example they may be prepared by oxidation of the corresponding indazole compounds of formula (II) of appropriate acid addition salts thereof

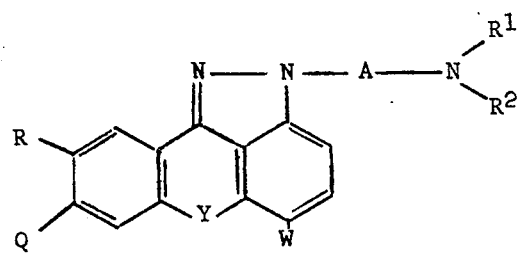

wherein A, $R^1$, $R^2$, W, Y, Q and R are as previously defined in formula (I). Oxidation is conveniently effected in an inert liquid medium by peroxides such as hydrogen peroxide or a peracid such as m-chloroperbenzoic acid, but other peracids such as peracetic, perphthalic and perbenzoic acid may also be used.

Suitable liquid media include protic and aprotic liquids such as lower alkanols, lower aliphatic halogenated hydrocarbons (for example dichloromethane or chloroform) and aliphatic ketones. The reactants are preferably allowed to react at room temperature but conversion to the compounds of formula (I) may, if desired, be performed at elevated temperatures.

The compounds of formula (I) may be isolated from the reaction mixture as the free base, or converted in situ into an acid addition salt, thereof. When isolated as the free base or an acid addition salt thereof, a compound of formula (I) may, if desired, be converted to a salt or another salt respectively by methods well known in the art. The acid addition salts are conveniently prepared by mixing the free base with at least an equivalent amount of the desired acid and precipitating the resulting acid addition salt with a solvent in which the salt is poorly soluble.

Acid addition salts of the compounds of formula (I) include salts of organic and inorganic acids, and except for formulation advantages, the choice of the acid for the purposes of the invention is not critical since the schistosomicidal activity lies in the free base. For medicinal purposes the salt must be pharmaceutically acceptable, but non-acceptable salts are also useful as intermediates for conversion to acceptable salts. Acid addition salts of the invention include salts of hydrochloric, hydrobromic, sulphuric, sulphamic, phosphoric, carbonic, succinic, citric, maleic, benzoic, acetic, benzenesulphonic, p-toluenesulphonic, methanesulphonic, and methylenebis (hydroxynaphthoic) acids.

The compounds of formula (I) and their pharmaceutically acceptable acid addition salts are useful in the treatment of schistosome infections of mammals, especially in the treatment of *S. haematobium* and *S. mansoni* infections. The optimum dose and route of administration of a compound of formula (I) will of course depend upon the nature and severity of the infection under treatment and the choice of the compound, but in general a dose of from 1 mg. to 100 mg. per kilogram body weight of the host animal may be used; preferably 1 to 25 mg. of compound per kg. of body weight orally over a 24 hour period, or 1 to 5 mg. per kg. of body weight parenterally, preferably intramuscularly, over a 24 hour period.

The N-oxides of the invention also showed a marked reduction in mutagenicity for *Salmonella* relative to the reference drug hycanthone. For example, when tested against *Salmonella* strain TA1583 (hisD3052 uvrBΔλ rfa) for drug-induced reversions by the method of Ames et al. [*Proc. Natl. Acad. Sci. U.S.A.*, 70, 2281 (1973)]. The compound of Example 1 was 250 times less mutagenic than hycanthone, while the compound of Example 2 was 70 times less mutagenic than hycanthone.

The compounds of formula (I) are conveniently presented for mammalian administration in the form of a pharmaceutical composition which includes a compound of formula (I) or an acid addition salt thereof, in association with a pharmaceutically acceptable carrier therefor. The carrier must of course be 'acceptable' in the sense of being compatible with the other ingredients of the composition and not deleterious to the recipient of the composition. The carrier may be a solid or a liquid, and is preferably formulated with a compound of formula (I) as a unit-dose composition for example a tablet. Other pharmacologically active substances may also be present in compositions of the present invention. The compounds of formula (I) may be incorporated in the compositions either in the form of the free base or an acid addition salt thereof, and the composition formulated by any of the well-known techniques of pharmacy consisting basically of admixture of the components of the composition.

For oral administration, powders or granules of a compound of formula (I) or a salt thereof may be associated with diluents, dispersing and surface active agents, and may be presented in a draft in water or in a syrup, in capsules or cachets in the dry state or in an aqueous or non-aqueous suspension, when a suspending agent may also be included; in tablets, preferably made from granules of the active ingredient with a diluent, by compression with binders and lubricants; or in a suspension in water or a syrup or an oil or in a water/oil emulsion, when flavouring, preserving, suspending, thickening and emulsifying agents may also be included. The granules or the tablets may be coated, and the tablets may be scored.

For parenteral administration, a compound of formula (I) or a salt thereof may be presented in unit dose or multi-dose containers in aqueous or non-aqueous injection solutions which may contain antioxidants, buffers, bacteriostats and solutes which render the compounds isotonic with the blood; or in aqueous or non-aqueous suspensions when suspending agents and thickening agents may also be included. Extemporaneous injection solutions and suspensions may be made from sterile powders, granules or tablets which may contain diluents, dispersing and surface active agents, binders and lubricants.

Included within the scope of the present invention are therefore:

a. Compounds of formula (I) and acid addition salts thereof, especially pharmaceutically acceptable acid addition salts.

b. The synthesis of the compounds of formula (I) and their salts by known methods, especially those described above.

c. Pharmaceutical compositions comprising an effective schistosomicidal amount of a compound of formula I or a pharmaceutically acceptable acid addition salt thereof, in association with a pharmaceutically acceptable carrier therefor.

d. A method for the treatment of schistosomiasis in a mammal comprising the administration to the mammal of an effective schistosomidicidal non-toxic amount of a compound of formula (I) or a pharmaceutically acceptable acid addition salt thereof.

Certain of the compounds of the invention can exist in anhydrous form as well as in solvated, including hydrated, forms. In general, the hydrated forms and the solvated forms with pharmaceutically-acceptable solvents are equivalent to the anhydrous or unsolvated form for the purposes of the invention.

The invention is illustrated by the following examples.

EXAMPLE 1 a. To a solution of 8-chloro-2-(2-(diethylamino)ethyl-5-methyl-2H(1)benzothiopyrano[4,3,2-cd]-indazole (1.86g.) in acetone (10 ml.) was added 2.1 ml. of 30% aqueous hydrogen peroxide and the mixture held at room temperature for 7 days. The solution was evaporated to dryness under reduced pressure and the resulting solid warmed with acetone (20 ml.). From the initial clear solution 8-chloro-2-(2-diethylamino)ethyl)-5-methyl-2H-(1)benzothiopyrano[4,3,2-cd]indazole N-oxide crystallized rapidly as the monohydrate, m.p. 139°–140° (decomp.).

By addition of one equivalent of methanesulphonic acid to an alcoholic solution of the base and subsequent dilution with ether, a methanesulphonate sale, m.p. 162° (decomp.) was obtained.

b. To a solution of 8-chloro-2-(2-(diethylamino)ethyl)-5-methyl-2H(1)benzothiopyrano[4,3,2-cd]-indazole (1.86g.) and m-chloroperbenzoic acid (1.05g. of 85% material) in ethanol (100 ml.) was added 40 ml. of a 0.4M. aqueous solution of potassium acetate. After standing at room temperature overnight the excess of ethanol was evaporated off under reduced pressure, 2% aqueous sodium carbonate was added and the basic material extracted with chloroform. Evaporation of the chloroform solution and crystallisation of the product from acetone gave crystals of the N-oxide monohydrate essentially identical with those described in (a) above.

EXAMPLE 2 a. To a solution of 8-chloro-2-(2-(diethylamino)ethyl)-5-hydroxymethyl-2H(1) benzothiopyrano[4,3,2-cd]indazole (1.94g.) and m-chloroperbenzoic acid (1.05g. of 85% material) in ethanol (100 ml.) was added a 0.4M. aqueous solution of potassium acetate (40 ml.). After standing at room temperature for 40 hours the pale yellow crystals which has separated were filtered off and washed with ethanol. These consisted of 8-chloro-2-(2-(diethylamino)ethyl)-5-hydroxymethyl-2H(1) benzothiopyrano[4,3,2-cd]indazole N-oxide, m.p. 187°–188° (decomp.)

By addition of one equivalent of methanesulphonic acid to an alcoholic solution of the base and subsequent dilution with ether, a methanesulphonate sale, m.p. 131°–133° (decomp.) was obtained.

b. A mixture of 8-chloro-2-(2-diethylamino)ethyl)-5-hydroxymethyl-2H(1)benzothiopyrano[4,3,2-cd]-indazole (1.94g.) in acetone (50 ml.) and 30% aqueous hydrogen peroxide (3.1 ml.) was held at 60°–65° for 15 hours. The separated crystals were collected by filtration, dissolved in a small volume of methanol and chloroform, and dry acetone added. The resulting crystals of N-oxide obtained were essentially identical with the material obtained by m-chloroperbenzoic acid oxidation above.

EXAMPLE 3

To a solution of 2-(2-diethylamino)ethyl)-5-methyl-2H(1)benzothiopyrano[4,3,2-cd]indazole (0.17g.) in acetone (4 ml.) was added 0.2 ml. of 30% aqueous hydrogen peroxide. The solution was left at room temperature overnight and then evaporated to dryness under reduced pressure. The residue was crystallized from acetone-ether to give 2-(2-(diethylamino)ethyl)-5-methyl-2H(1) benzothiopyrano[4,3,2-cd]indazole N-oxide monohydrate, m.p. 123° – 124° (decomp.). This compound, when crystallized in the presence of hydrochloric acid, gave a water-soluble monohydrochloride salt which darkened and decomposed at temperatures above 150°.

EXAMPLE 4

To a solution of 2-(2-diethylamino)ethyl)-2H-(1)benzothiopyrano[4,3,2-cd]indazole-5-methanol (0.18g.) in acetone (3 ml.) was added 30% aqueous hydrogen peroxide (0.21 ml.) and the mixture left overnight at room temperature. Evaporation under reduced pressure and crystallization from ethanol-ethyl acetate gave 2-(2-diethylamino)ethyl-2H(1)benzothiopyrano[4,3,2-cd]indazole-5-methanol N-oxide one-third hydrate which melted at 142° – 143°(decomp.).

EXAMPLE 5

By condensation of 1-chloro-4-methyl-9-xanthenone with 2-(dimethylamino)ethylhydrazine was obtained 2-(2-(dimethylamino)ethyl)-5-methyl-2H(1)benzopyrano[4,3,2-cd]indazole. To 0.11 g. of this base in ethanol (10 ml.) was added 30% aqueous hydrogen peroxide (0.2 ml.). After 22 hours at room temperature the solution was evaporated to dryness under reduced pressure and the residue crystallized from ethanol-ether to give 2-(2-(dimethylamino)ethyl)-5-methyl-2H(1)benzopyrano[4,3,2-cd]indazole N-oxide sesquihydrate, m.p. 139° – 140° (decomp.).

EXAMPLE 6

To a solution of 8-chloro-2-(2-(isopropylmethylamino)ethyl)-5-methyl-2H(1)benzothiopyrano[4,3,2-cd]indazole (0.19 g.) in acetone (3 ml.) was added 0.25 ml. of 30% aqueous hydrogen peroxide and the mixture was kept at room temperature for 4 days. The solid obtained on evaporation of the solution under reduced pressure was crystallized from ethanol-ether to give 8-chloro-2-(2-(isopropylmethylamino)ethyl)-5-methyl-2H(1)benzothiopyrano[4,3,2-cd]indazole N-oxide monohydrate, m.p 132° – 133° (decomp.).

EXAMPLE 7

By a method similar to that described in Example 4, 8-chloro-5-methyl-2-(3-(1-pyrrolidinyl)propyl)-2H(1)-benzothiopyrano[4,3,2-cd]indazole was converted in the corresponding N-oxide which crystallized from ethanolether as the hydrate, m.p. 146° – 147° (decomp.).

EXAMPLE 8

By a method similar to that described in Example 4, 8-chloro-5-methyl-2-(3-piperidinopropyl)-2H(1)benzothiopyrano]4,3,2-cd]indazole was converted into the corresponding N-oxide which crystallized from acetone as the monohydrate, m.p. 137° – 138° (decomp.).

EXAMPLE 9

To a solution of 8-chloro-2-(2-(diethylamino)ethyl)-2H(1)benzothiopyrano[4,3,2-cd]indazole-5-methyl acetate ester (0.18 g.) in ethanol (3 ml.) was added 30% aqueous hydrogen peroxide (0.22 ml.). After 1 day crystals of starting material had separated from the solution; these were redissolved by gentle warming and the solution kept at room temperature for a further 4 days. Evaporation to dryness under reduced pressure gave a solid which, when crystallized from ethanol-ether, yielded crystals m.p. 145° (decomp.) consisting of 8-chloro-2-(2-(diethylamino)ethyl)-2H(1)benzothiopyrano[4,3,2-cd]indazole-5-methyl acetate ester N-oxide sesquihydrate.

The starting material is prepared in the following manner:

To a solution of 0.4 g. of 8-chloro-2-(2-(diethylamino)ethyl)-5-hydroxymethyl-2H(1)benzothiopyrano[4,3,2-cd]indazole in pyridine was added 0.3 ml. of acetic anhydride. After heating on a steam bath for 15 minutes, the reaction mixture was cooled and diluted with ether, whereupon the desired 8-chloro-2-(2-(diethylamino)ethyl)-5-hydroxymethyl-2H(1)benzothiopyrano[4,3,2-cd]indazole acetate ester separated and was collected by filtration.

EXAMPLE 10

By the condensation of 1-chloro-6-methoxy-4-methyl-9-thioxanthenone with 2-(diethylamino)ethylhydrazine was obtained 2-(2-(diethylamino)ethyl)-8-methoxy-5-methyl-2H(1)benzothiopyrano[4,3,2-cd]indazole. To 0.18g. of this base in acetone (3 ml.) was added 30% aqueous hydrogen peroxide (0.22 ml.). After standing at room temperature for 90 hours the solution was evaporated under reduced pressure. The solid residue gave crystals m.p. 132° – 133° (decomp.) from acetone which consisted of 2-(2-(diethylamino)ethyl)-8-methoxy-5-methyl-2H(1)benzothiopyrano[4,3,2-cd]indazole N-oxide 1.75 hydrate.

EXAMPLE 11

By the condensation of 1-chloro-6-methoxy-4-methyl-9-xanthenone with 2-(diethylamino)ethyl) hydrazine was obtained 2-(2-(diethylamino)ethyl)-8-methoxy-5-methyl-2H(1)benzopyrano[4,3,2-cd]indazole. To 0.27 g. of this base in acetone (4 ml.) was added 30% aqueous hydrogen peroxide (0.35 ml.). After standing for 90 hours at room temperature the solution was evaporated under reduced pressure. Addition of ether to an ethanolic solution of the residue gave an oil which slowly crystallized. Further crystallization from acetonitrile gave yellow crystals m.p. 132° – 133° (decomp.) of 2-(2-(diethylamino)ethyl)-8-methoxy-5-methyl-2H(1)benzopyrano[4,3,2-cd]indazole N-oxide 1.75 hydrate.

EXAMPLE 12

By condensation of 1,7-dichloro-4-methyl-9-thioxanthenone with 2-(diethylamino)ethyl hydrazine was obtained 9-chloro-2-(2-(diethylamino)ethyl)-5-methyl-2H-(1)benzothiopyrano[4,3,2-cd]indazole. To 0.13 g. of this base in acetone (3 ml.) was added 30% aqueous hydrogen peroxide (0.2 ml.). After 18 hours at room temperature the solution was evaporated to dryness under reduced pressure and the residue crystallized from acetone to give 9-chloro-2-(2-diethylamino)ethyl)-5-methyl-2H(1)-benzothiopyrano[4,3,2-cd]indazole N-oxide monohydrate, m.p. 134° – 135° (decomp.).

EXAMPLE 13

The compounds of Example 1 and 2 were administered to mice having 9-week mature infections of *Schistosoma mansoni*. The animals were autopsied at 12 and 21 days after completion of treatment, and the results obtained in treated animals were compared with controls. The results are shown in the following Table.

Table

| Compound administered | Administration route | Dose (mg./kg.) | Autopsy post treatment (days) | % Kill of flukes |
| --- | --- | --- | --- | --- |
| Example 1 (base) | Oral | 100 twice daily for five days | 12 | 99 |
| Example 2 (base) | Oral | 100 twice daily for five days | 12 | 100 |
| Example 1 (salt) | Intramuscular | 50 single dose | 21 | 87 |
| Example 2 (salt) | Intramuscular | 50 single dose | 21 | 86 |

I claim:
1. A compound of the formula

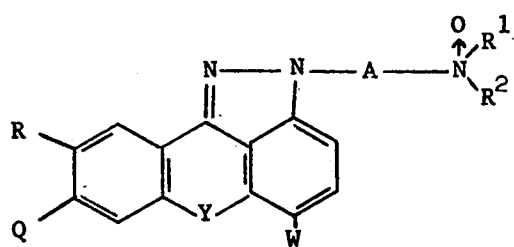

and acid addition salts thereof; wherein:
A is an alkylene radical containing 2 to 4 carbon atoms;
$R^1$ and $R^2$ are the same or different and represent $C_1$ – $C_4$ alkyl;
W is methyl, hydroxymethyl or acyloxymethyl wherein said acyl fragment contains from one to eight carbon atoms,
Y is sulfur or oxygen; and
one of Q and R is hydrogen and the other is hydrogen, halo or alkoxy having from one to four carbon atoms.

2. The compound of claim 1 wherein Y is sulfur.
3. The compound of claim 2 wherein W is hydroxymethyl.
4. The compound of claim 2 which is 8-Chloro-2-(2-(diethylamino)ethyl)-5-methyl-2H(1)benzothiopyrano[4,3,2-cd]indazole N-oxide and acid addition salts thereof.
5. The compound of claim 2 which is 8-Chloro-2-(2-(diethylamino)ethyl)-5-hydroxymethyl-2H(1)benzothiopyrano[4,3,2-cd]indazole N-oxide and acid addition salts thereof.
6. The compound of claim 2 which is 2-(2-(diethylamino)ethyl)-5-methyl-2H(1)benzothiopyrano[4,3,2-cd]indazole N-oxide and acid addition salts thereof.
7. The compound of claim 2 which is 2-(2-(diethylamino)ethyl)-8-methoxy-5-methyl-2H-(1)benzothiopyrano[4,3,2-cd]indazole N-oxide and acid addition salts thereof.
8. The compound of claim 2 which is 2-(2-(diethylamino)ethyl)-8-methoxy-5-methyl-2H-(1)benzopyrano[4,3,2-cd]indazole N-oxide and acid addition salts thereof.

* * * * *